(12) United States Patent
Franke et al.

(10) Patent No.: US 9,370,659 B2
(45) Date of Patent: Jun. 21, 2016

(54) INTUITED DELIVERY OF AUTONOMIC MODULATION THERAPY

(71) Applicant: Cardiac Pacemakers, Inc., St. Paul, MN (US)

(72) Inventors: Manfred Franke, Weissenborn Sa. (DE); Stephen B. Ruble, Lino Lakes, MN (US); David J. Ternes, Roseville, MN (US); Juan Gabriel Hincapie Ordonez, Maple Grove, MN (US); Jason J. Hamann, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 14/557,707

(22) Filed: Dec. 2, 2014

(65) Prior Publication Data

US 2015/0157868 A1    Jun. 11, 2015

Related U.S. Application Data

(60) Provisional application No. 61/912,315, filed on Dec. 5, 2013.

(51) Int. Cl.
*A61N 1/372*      (2006.01)
*A61N 1/36*      (2006.01)

(52) U.S. Cl.
CPC ........ *A61N 1/36114* (2013.01); *A61N 1/36175* (2013.01); *A61N 1/36178* (2013.01); *A61N 1/36117* (2013.01)

(58) Field of Classification Search
CPC ............ A61N 1/0551; A61N 1/36139; A61N 1/36135; A61N 1/36167; A61N 1/3702; A61N 1/3605; A61N 1/37; A61N 1/365; A61N 1/36146; A61N 1/08; A61N 1/36178; A61B 5/4035; A61B 5/024; A61B 5/0452; A61B 5/4836
See application file for complete search history.

(56) References Cited

U.S. PATENT DOCUMENTS 7,321,793 B2   1/2008   Ben Ezra et al.
7,542,800 B2   6/2009   Libbus et al.
(Continued)

FOREIGN PATENT DOCUMENTS

WO    WO-03099377 A1    12/2003
WO    WO-2015084774 A1    6/2015

OTHER PUBLICATIONS

Barrett, D. J., et al., "Spontaneous efferent activity in branches of the vagus nerve controlling heart rate and ventilation in the dogfish", J. exp. Biol. 117, (1985), 433-448.
Green, J. H., et al., "Studies Upon the Relationship Between Baroreceptor and Sympathetic Activity", Q. Jl exp. Physiol. (1968) 53, (1968), 23-32.
Sung J., et al., "Exercise blood pressure response is related to left ventricular mass", Journal of Human Hypertension (2003) 17, 333-338, (2003), 333-338.
(Continued)

*Primary Examiner* — Deborah Malamud
(74) *Attorney, Agent, or Firm* — Schwegman Lundberg & Woessner, P.A.

(57) ABSTRACT

An example of a method embodiment may deliver intermittent neural stimulation (INS) therapy to an autonomic neural target of a patient. The INS therapy includes neural stimulation (NS) ON times alternating with NS OFF times, and includes at least one NS burst of NS pulses during each of the NS ON times. For a given NS OFF time and subsequent NS ON time, delivering INS therapy may include monitoring a plurality of cardiac cycles during the NS OFF time, using the monitored plurality of cardiac cycles to predict cardiac event timing during the subsequent NS ON time, and controlling delivery of the INS therapy using the predicted cardiac event timing to time NS burst delivery of at least one NS burst for the subsequent NS ON time based on the predicted cardiac event timing.

20 Claims, 11 Drawing Sheets

(56) References Cited

U.S. PATENT DOCUMENTS

| | | |
|---|---|---|
| 7,974,693 B2 * | 7/2011 | Ben-David et al. ............ 607/17 |
| 8,219,188 B2 | 7/2012 | Craig |
| 8,285,373 B2 | 10/2012 | Ternes et al. |
| 8,805,502 B2 | 8/2014 | Ternes et al. |
| 2006/0224188 A1 | 10/2006 | Libbus et al. |
| 2012/0185010 A1 | 7/2012 | Zhou et al. |
| 2015/0157867 A1 | 6/2015 | Ternes et al. |

OTHER PUBLICATIONS

"U.S. Appl. No. 14/557,667, Non Final Office Action mailed Aug. 20, 2015", 8 pgs.

"International Application Serial No. PCT/US2014/068028, International Search Report mailed Feb. 16, 2015", 3 pgs.

"International Application Serial No. PCT/US2014/068028, Written Opinion mailed Feb. 16, 2015", 3 pgs.

\* cited by examiner

US 9,370,659 B2

INTUITED DELIVERY OF AUTONOMIC MODULATION THERAPY

CLAIM OF PRIORITY

This application claims the benefit of priority under 35 U.S.C. §119(e) of U.S. Provisional Patent Application Ser. No. 61/912,315, filed on Dec. 5, 2013, which is herein incorporated by reference in its entirety.

TECHNICAL FIELD

This document relates generally to medical devices, and more particularly, to systems, devices and methods for delivering electrical stimulation.

BACKGROUND

Neural stimulation has been proposed as a therapy for a number of conditions. Neural stimulation may be delivered to modulate the autonomic system, which may be referred to as an autonomic modulation therapy (AMT). Examples of AMT include therapies for respiratory problems such as sleep disordered breathing, blood pressure control such as to treat hypertension, cardiac rhythm management, myocardial infarction and ischemia, heart failure (HF), epilepsy, depression, pain, migraines, eating disorders and obesity, and movement disorders. It has been proposed to deliver bursts of neural stimulation pulses synchronized to a cardiac cycle. However, it may be difficult to accurately sense cardiac activity during the AMT because, due to limitations in an implanted system, it can be technically challenging for the sensing circuitry to consistently detect cardiac activity while the therapy circuitry of the system is delivering a burst.

SUMMARY

Various embodiments provided herein may deliver AMT as an intermittent neural stimulation therapy where burst of neural stimulation are synchronized to predicted cardiac event timing within cardiac cycles. For example, a method embodiment may deliver intermittent neural stimulation (INS) therapy to an autonomic neural target of a patient. The INS therapy includes neural stimulation (NS) ON times alternating with NS OFF times, and includes at least one NS burst of NS pulses during each of the NS ON times. For a given NS OFF time and subsequent NS ON time, delivering INS therapy may include monitoring a plurality of cardiac cycles during the NS OFF time, using the monitored plurality of cardiac cycles to predict cardiac event timing during the subsequent NS ON time, and controlling delivery of the INS therapy using the predicted cardiac event timing to time NS burst delivery of at least one NS burst for the subsequent NS ON time based on the predicted cardiac event timing.

An example of a system embodiment for delivering neural stimulation to an autonomic neural target of a patient may include a cardiac cycle monitor configured to monitor cardiac cycles, a neural stimulator configured to deliver neural stimulation to the autonomic neural target, and a controller. The controller may be configured to control the neural stimulator to deliver INS therapy to the autonomic neural target. The INS therapy includes NS ON times alternating with NS OFF times. In delivering INS therapy the controller and the neural stimulator may cooperate to deliver at least one NS burst of NS pulses during each of the NS ON times. The controller, the neural stimulator and the cardiac cycle monitor may be configured to cooperate to implement a process to control NS burst timing where the process may include monitoring a plurality of cardiac cycles during a given NS OFF time, using the monitored plurality of cardiac cycles during the given NS OFF time to predict cardiac event timing during a subsequent NS ON time, and controlling delivery of the INS therapy using the predicted cardiac event timing to time NS burst delivery of at least one NS burst for the subsequent NS ON time based on the predicted cardiac event timing.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
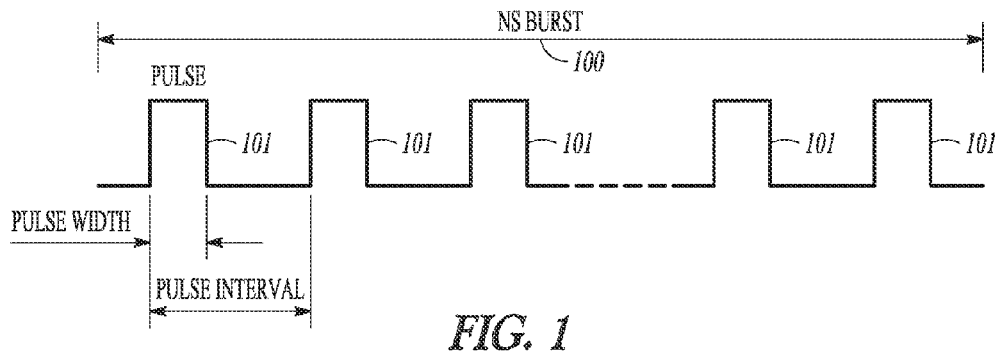
FIG. 1 illustrates an example of an NS burst of NS pulses.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. For example, neural stimulation as used herein may refer to stimulation that elicits nerve traffic in a neural target. However, a neural target may be stimulated with appropriate stimulation parameters to reduce or block nerve traffic at the neural target. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Neural stimulation may be delivered to stimulate the autonomic nervous system (ANS). For example, the neural stimulation may be directed to stimulating a vagus nerve in the neck (e.g. cervical vagus nerve) or to stimulating various nerves that branch from the vagus nerve trunk. The neural stimulation may be directed to other ANS targets. Examples of other autonomic neural stimulation targets include but are not limited to baroreceptor regions such as may be found in the carotid sinus region or in the pulmonary artery, chemoreceptor regions, the glossopharyngeal nerve, the carotid sinus nerve, and spinal nerves. The ANS regulates "involuntary" organs. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscles around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent neurons convey impulses towards the central nervous system (CNS), and efferent neurons convey impulses away from the CNS.

Stimulating the sympathetic and parasympathetic nervous systems can cause heart rate, blood pressure and other physiological responses. For example, stimulating the sympathetic nervous system may dilate the pupil, reduce saliva and mucus production, relax the bronchial muscle, reduce the successive waves of involuntary contraction (peristalsis) of the stomach and the motility of the stomach, increase the conversion of glycogen to glucose by the liver, decrease urine secretion by the kidneys, and relax the wall and closes the sphincter of the bladder. Stimulating the parasympathetic nervous system (inhibiting the sympathetic nervous system) may constrict the pupil increase saliva and mucus production, contract the bronchial muscle, increase secretions and motility in the stomach and large intestine, increase digestion in the small intestine, increase urine secretion, and contract the wall and relax the sphincter of the bladder. The functions associated with the sympathetic and parasympathetic nervous systems are many and can be complexly integrated with each other. A therapy which intentionally affects the parasympathetic activity and/or sympathetic activity within the ANS may be referred to as an Autonomic Modulation Therapy (AMT). A neural stimulation therapy delivered to an autonomic neural target is an example of an AMT. The vagus nerve is an example of an autonomic neural target. For example, the cervical vagus nerve may be stimulated to treat conditions such as, by way of example and not limitation, hypertension, heart failure, arrhythmias and pain. Other examples of conditions that may be treatable using vagus nerve stimulation include, but are not limited to, migraines, eating disorders, obesity, inflammatory diseases, and movement disorders. Other autonomic neural targets include, but are not limited to, baroreceptor regions, chemoreceptor regions, cardiac fat pads, various branches of the vagus nerve, the carotid sinus nerve, and the glossopharyngeal nerve. The carotid sinus region, for example, includes the carotid body near the bifurcation of the carotid artery. The carotid body includes a cluster of chemoreceptors. The carotid sinus region also includes baroreceptors.

A reduction in parasympathetic nerve activity contributes to the development and progression of a variety of cardiovascular diseases. Some embodiments of the present subject matter can be used to prophylactically or therapeutically treat various cardiovascular diseases by modulating autonomic tone. Neural stimulation to treat cardiovascular diseases may be referred to as neurocardiac therapy (NCT). Vagal stimulation used to treat cardiovascular diseases may be referred to as either vagal stimulation therapy (VST) or NCT. However, VST may be delivered for non-cardiovascular diseases, and NCT may be delivered by stimulating a nerve other than the vagal nerve. Examples of cardiovascular diseases or conditions that may be treated using AMT include hypertension, HF, and cardiac remodeling. These conditions are briefly described below.

Hypertension is a cause of heart disease and other related cardiac co-morbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

HF refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. HF can be due to a variety of etiologies such as ischemic heart disease. HF patients have impaired autonomic balance, which is associated with LV dysfunction and increased mortality.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

It has been proposed to deliver bursts of neural stimulation pulses synchronized to a cardiac cycle. One example of such a system is provided in U.S. application Ser. No. 61/912,274) filed on the same date as the present application, and entitled "Dosed Delivery of Autonomic Modulation Therapy", which application is incorporated by reference herein in its entirety. Thus, for example, various embodiments described herein may deliver AMT as a dose per cardiac cycle.

Various embodiments described herein may deliver AMT within an intuited or predicted window that encompasses a desired timeframe within the cardiac cycle. As the delivering of the NS burst is based on an estimated cardiac event timing the delivery of the NS burst is not triggered by the actual detection of the cardiac event timing. It is believed that such delivery of AMT may maintain the efficacy of the AMT while reducing overall power consumption of the device delivering AMT. The cardiac cycle does not have a "vulnerable" period for delivering the AMT, but AMT may be more effective during a certain time period within the cardiac cycle. Therefore, it is believed that there may be benefits for delivering the stimulation during this target window within the cardiac cycle, but it is also believed that there is no extreme harm if the estimated timing is off. Furthermore, cardiac cycle sensing without intracardiac leads may be used to accurately detect the cardiac cycles during stimulation OFF times. This cardiac sensing can be used to time the stimulation during stimulation ON times. Systems and implantation procedures may be simpler without introducing an intra-cardiac sensing lead. As the stimulation is timed to occur during the more effective portions of the cardiac cycle, the overall number of pulses delivered as part of the AMT may be reduced, which may increase the tolerance of the stimulation in addition to lowering the energy used by the system.

The cardiac cycle during the stimulation OFF times may be monitored using a variety of means, such of the use of sensing electrodes with a wide sense vector for remotely sensing cardiac activity, heart sounds carotid pulse pressure, cardiac sensing lead, and the like. Electrodes on lead(s) and/or electrode(s) on the implantable housing may be used to sense cardiac activity. U.S. Pat. No. 8,285,373, entitled "Remote Sensing in an Implantable Medical Device", provides some examples and is incorporated herein by reference in its entirety. Some embodiments may use an average heart rate over the course of two or more cardiac cycles to estimate the cardiac event timing for subsequent cardiac cycles. The average may be based on the entirety of the OFF portion of the duty cycle, or may be based only on the last few cardiac cycles for the OFF portion. By way of example and not limitation, the average may be taken from the last four cardiac cycles before the next ON portion of the duty cycle. This may correspond to the last four or five seconds of the OFF portion of the duty cycle. This limited sensing may improve longevity of an implanted device.

One way to maintain accurate estimates is to reduce the number of cardiac cycles within the Stimulation ON portion. Thus, by way of example, INS maybe delivered with a 10 second ON/50 second OFF duty cycle. Delivering INS with a 1 second ON 5 second off second may maintain a more accurate estimation as there are fewer events to be estimated, and the time from the last measured event timing to the predicted event is shorter.

FIG. 1 illustrates an example of an NS burst 100 of NS pulses 101. The NS burst 100 has a number of NS pulses 101, which can be delivered during a cardiac cycle. The NS pulses delivered within the burst may have a consistent pulse width and a repeated pulse interval. Those of ordinary skill in the art will appreciate that the pulse interval may be referred to as a pulse frequency as a pulse occurs after a period of time (e.g. pulse period=1/pulse frequency). The illustrated pulses also have an amplitude. The intensity of neural stimulation is affected by the amount of charge delivered to the target, as well as the density of the charge delivered to the target during the period of time. This amount of charge depends on the amplitude, the pulses width, and the pulse frequency of the pulses affect the amount of delivered charge, and thus can affect the dose.

Figure 2:
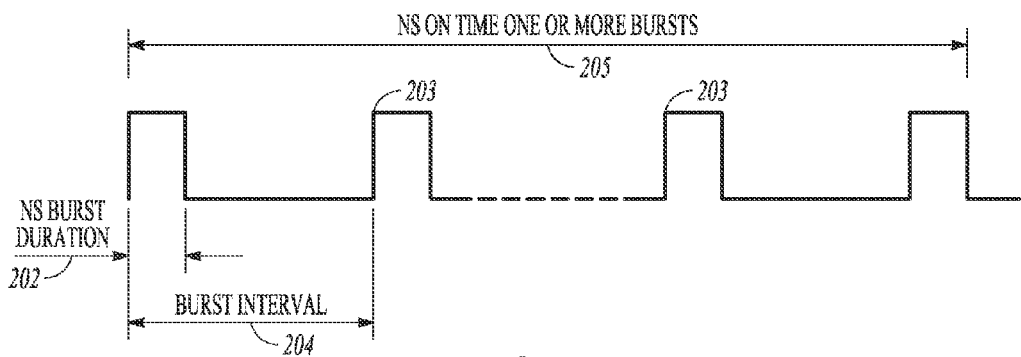
FIG. 2 illustrates a representation of intermittent neural stimulation (INS).

FIG. 2 illustrates a representation of intermittent neural stimulation (INS). The figure diagrammatically shows the time-course of a neural stimulation that alternates between intervals of stimulation being ON, when one stimulation pulse or a set of grouped stimulation pulses (i.e., a burst 200) is delivered, and intervals of stimulation being OFF, when no stimulation pulses are delivered. Thus, for example, some embodiments deliver a plurality of monophasic or biphasic pulses within a neural stimulation burst 200. The duration of the stimulation ON interval is sometimes referred to as the stimulation duration or burst duration 202. The burst duration also affects the dose of the neural stimulation therapy. The start of a stimulation ON interval is a temporal reference point NS Event 203. The NS Event may be a sensed event or derived from a sensed event or a programmed time. The time interval between successive NS Events is the INS Interval 204, which is sometimes referred to as the stimulation period or burst period. The burst period or the number of neural stimulation events that occur over a time period also affect the dose of the neural stimulation. For an application of neural stimulation to be intermittent, the stimulation duration 202 is less than the stimulation period (i.e., INS Interval 204). The duration of the OFF intervals of INS are determined by the durations of the ON interval and the INS Interval. The duration of the ON interval relative to the INS Interval (e.g., expressed as a ratio) is sometimes referred to as the duty cycle of the INS. The present subject matter may deliver a burst of NS pulses within a cardiac cycle, and may further deliver the burst of NS pulses timed to an estimated time within the cardiac cycle. One or more bursts of NS pulses may be delivered during a NS ON time 205.

Figure 3:
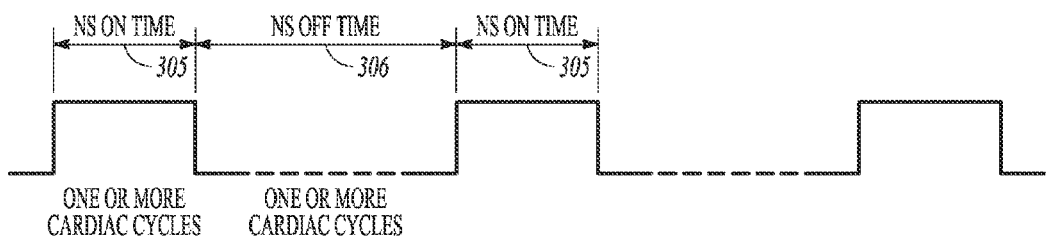
FIG. 3 illustrates a representation for an example of an additional layer of ON/OFF timing for neural stimulation.

FIG. 3 illustrates a representation for an example of an additional layer of ON/OFF timing for the neural stimulation. By way of example and not limitation, the INS illustrated in FIG. 2 as being delivered during NS ON time 205 may be delivered during NS ON times 305 over one or more cardiac cycles. These NS ON times 305 are separated by NS OFF times 306 with no NS pulses. These NS OFF times may have a duration of one or more cardiac cycles.

U.S. Pat. No. 7,542,800, entitled "Method and Apparatus for Synchronizing Neural Stimulation to Cardiac Cycles", assigned to Cardiac Pacemakers, Inc." discusses and example for synchronizing neural stimulation to cardiac cycle. U.S. Pat. No. 7,542,800 is incorporated by reference in its entirety. The present subject matter can be implemented within such a system, as it estimates event timing within the cardiac cycle, and synchronizes stimulation to the estimated event timing.

Figure 4:
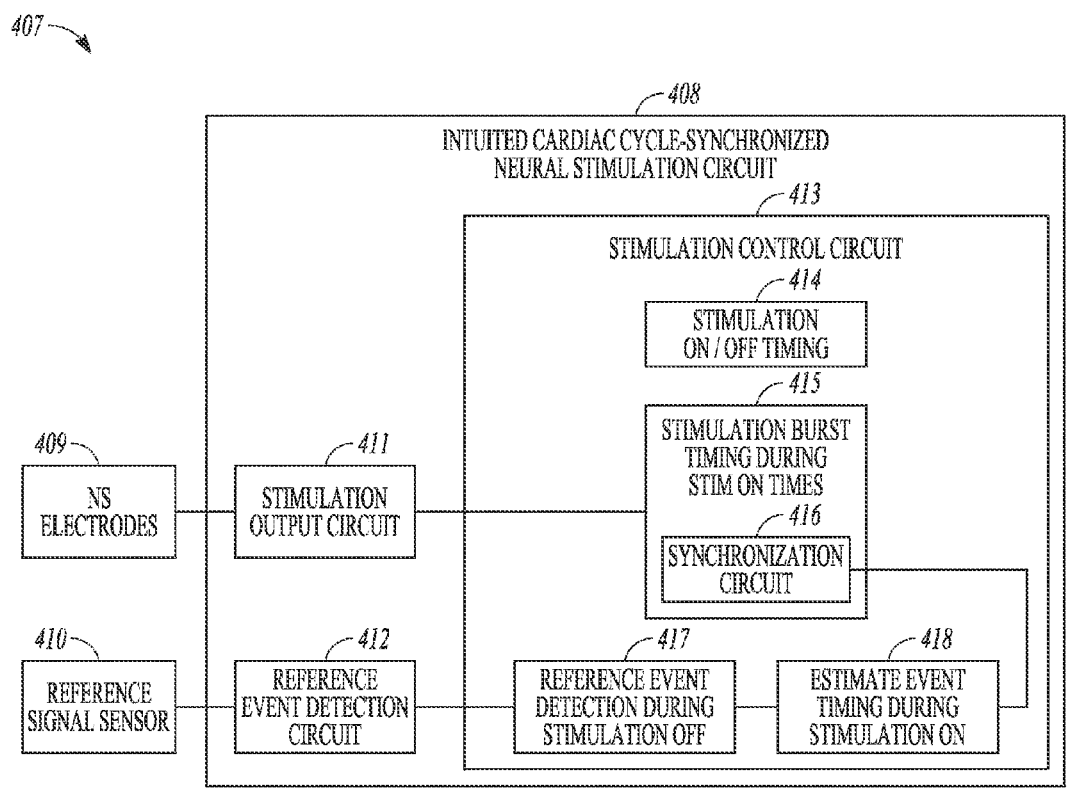
FIG. 4 illustrates, by way of example, an embodiment of a system for synchronizing neural stimulation using estimated event timing within the cardiac cycle.

FIG. 4 illustrates, by way of example, an embodiment of a system for synchronizing neural stimulation using estimated event timing within the cardiac cycle. The illustrated system 407 may be an implantable device. The illustrated system 407 may include a intuited cardiac cycle-synchronized neural stimulation circuit 408, NS electrodes 409 for use in delivering neural stimulation, and a reference signal sensor 410 for use in detecting a reference within a cardiac cycle.

The reference signal sensor 410 senses a reference signal indicative of cardiac cycles. The reference signal sensor 410 may be an implantable reference signal sensor. The timing reference event is a recurring feature of the cardiac cycle that is chosen to be a timing reference to which the neural stimulation is synchronized. The reference signal sensor 410 may be configured for extracardiac and extravascular placement, i.e., placement external to the heart and blood vessels. Examples of reference signal sensors may include a set of electrodes for sensing a subcutaneous ECG signal, an acoustic sensor for sensing an acoustic signal indicative of heart sounds, and a hemodynamic sensor for sensing a hemodynamic signal indicative of hemodynamic performance. The system 407 may have an implantable housing that contains both a reference signal sensor 410 and the intuited cardiac cycle-synchronized neural stimulation circuit 408. In an embodiment, the reference signal sensor 410 is incorporated onto the implantable housing. In an embodiment, the reference signal sensor 410 is electrically connected to the system 407 through one or more leads. In an embodiment, the reference signal sensor 410 may be communicatively coupled to the system 407 via an intra-body telemetry link.

The intuited cardiac cycle-synchronized neural stimulation circuit 408 may include a stimulation output circuit 411, a reference event detection circuit 412, and a stimulation control circuit 413. The reference event detection circuit 412 receives the reference signal from the reference signal sensor 410 and detects the timing reference event from the reference signal. The stimulation control circuit 413 controls the delivery of the neural stimulation pulses and includes a stimulation ON/OFF timing module 414, a stimulation burst timing module 415 with a synchronization circuit 416 to control burst timing during stimulation ON times. The stimulation control circuit 413 may further include a reference event detection module 417 configured to detect reference events during stimulation OFF times, and an estimate event timing module 418 configured to predict, based on the detected reference events during stimulation OFF times, event timing to cardiac cycle(s) during the stimulation ON times. The synchronization circuit 416 may be configured to receive a signal from module 418 to identify an event timing estimate, and use that event timing estimate to time delivery of the neural stimulation pulses. The stimulation output circuit 411 may be configured to deliver neural stimulation pulses upon receiving a pulse delivery signal from the stimulation burst timing module 415.

The system may incorporate additional sensors and/or may include a circadian rhythm timer. For example, the system may include an activity sensor and include an activity discriminator to determine an activity level based on the output from the activity sensor(s). The activity sensor and activity discriminator may be used to refine the estimated event timing. The circadian rhythm timer may be used to refine the estimated event timing. Furthermore, the sensed activity and circadian rhythm may be used to adjust the dose of the neural stimulation.

In some embodiments, the system may include a respiratory sensor, and the system may be configured to time delivery of neural stimulation pulses to decrease sympathetic activity during the inspiratory phase, and time delivery of neural stimulation pulses to increase parasympathetic activity during the expiratory phase. The respiration sensor can be used to guide the neural stimulation reduce sympathetic activity during the inspiratory phase when sympathetic activity is intrinsically high, and/or to enhance parasympathetic activity during an expiratory phase.

Figure 5:
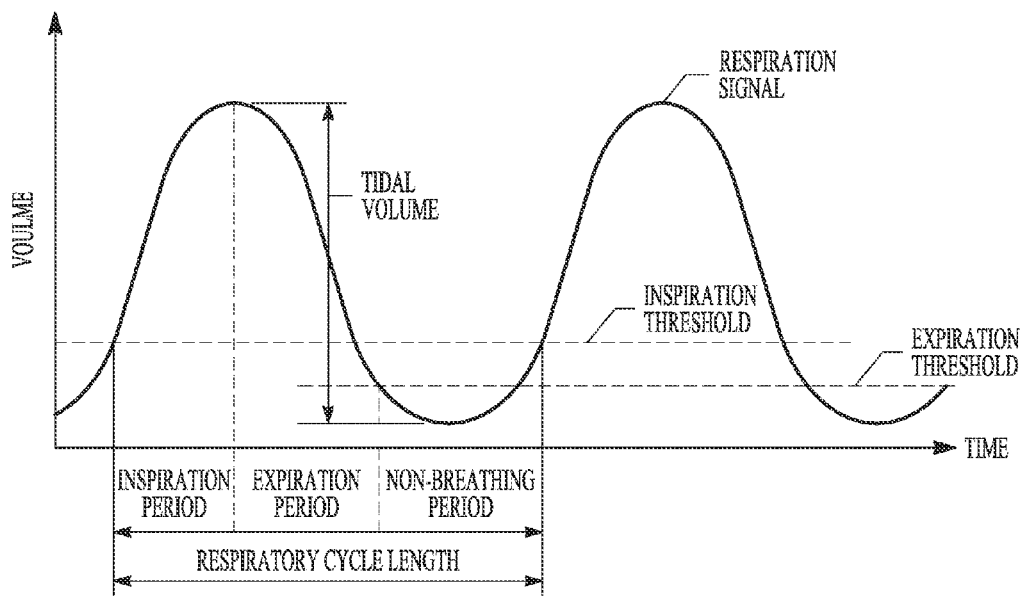
FIG. 5 is an illustration of a respiratory signal indicative of respiratory cycles and respiratory parameters including respiratory cycle length, inspiration period, expiration period, non-breathing period, and tidal volume.

FIG. 5 is an illustration of a respiratory signal indicative of respiratory cycles and respiratory parameters including respiratory cycle length, inspiration period, expiration period, non-breathing period, and tidal volume. The inspiration period starts at the onset of the inspiration phase of a respiratory cycle, when the amplitude of the respiratory signal rises above an inspiration threshold, and ends at the onset of the expiration phase of the respiratory cycle, when the amplitude of the respiratory cycle peaks. The expiration period starts at the onset of the expiration phase and ends when the amplitude of the respiratory signal falls below an expiration threshold. The non-breathing period is the time interval between the end of the expiration phase and the beginning of the next inspiration phase. The tidal volume is the peak-to-peak amplitude of the respiratory signal.

Figure 6:
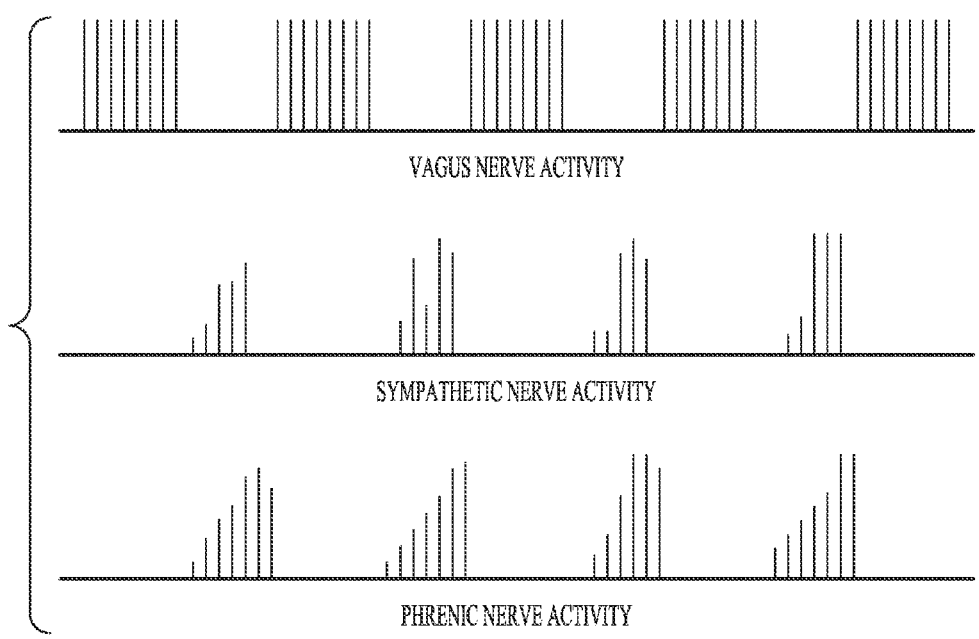
FIG. 6 illustrates the relationship between respiration, as illustrated by phrenic nerve activity, and both sympathetic nerve activity and vagus nerve activity.

FIG. 6 illustrates the relationship between respiration, as illustrated by phrenic nerve activity, and both sympathetic nerve activity and vagus nerve activity. Vagus nerve activity is parasympathetic. As illustrated, sympathetic nerve activity is most active during periods where the phrenic nerve activity is active, and parasympathetic nerve activity is most active during periods when the phrenic nerve activity is inactive.

According to some embodiments, timing is provided to deliver neural stimulation pulses to decrease sympathetic activity during the inspiratory phase and/or to deliver neural stimulation pulses to increase parasympathetic activity during the expiratory phase. For some embodiments, timing is provided to deliver neural stimulation pulses to decrease sympathetic activity during the expiratory phase, and/or deliver neural stimulation pulses to increase parasympathetic activity during the inspiratory phase.

The respiratory signal is a physiologic signal indicative of respiratory activities. In various embodiments, the respiratory signal may include any physiology signal that is modulated by respiration. In one embodiment, the respiratory signal may include a transthoracic impedance signal sensed by an implantable impedance sensor. In another embodiment, the respiratory signal may be extracted from a blood pressure signal that is sensed by an implantable pressure sensor and includes a respiratory component. In another embodiment, the respiratory signal may be sensed by an external sensor that senses a signal indicative of chest movement or lung volume. According to various embodiments, peaks of a respiratory signal are detected as respiratory fiducial points. A delay interval starts upon the detection of each of peaks. A burst of neural stimulation pulses is delivered to a neural target when delay interval expires. In various other embodiments, onset points of the inspiration phases, ending points of the expiration phases, or other threshold-crossing points are detected as the respiratory fiducial points.

Figure 7:
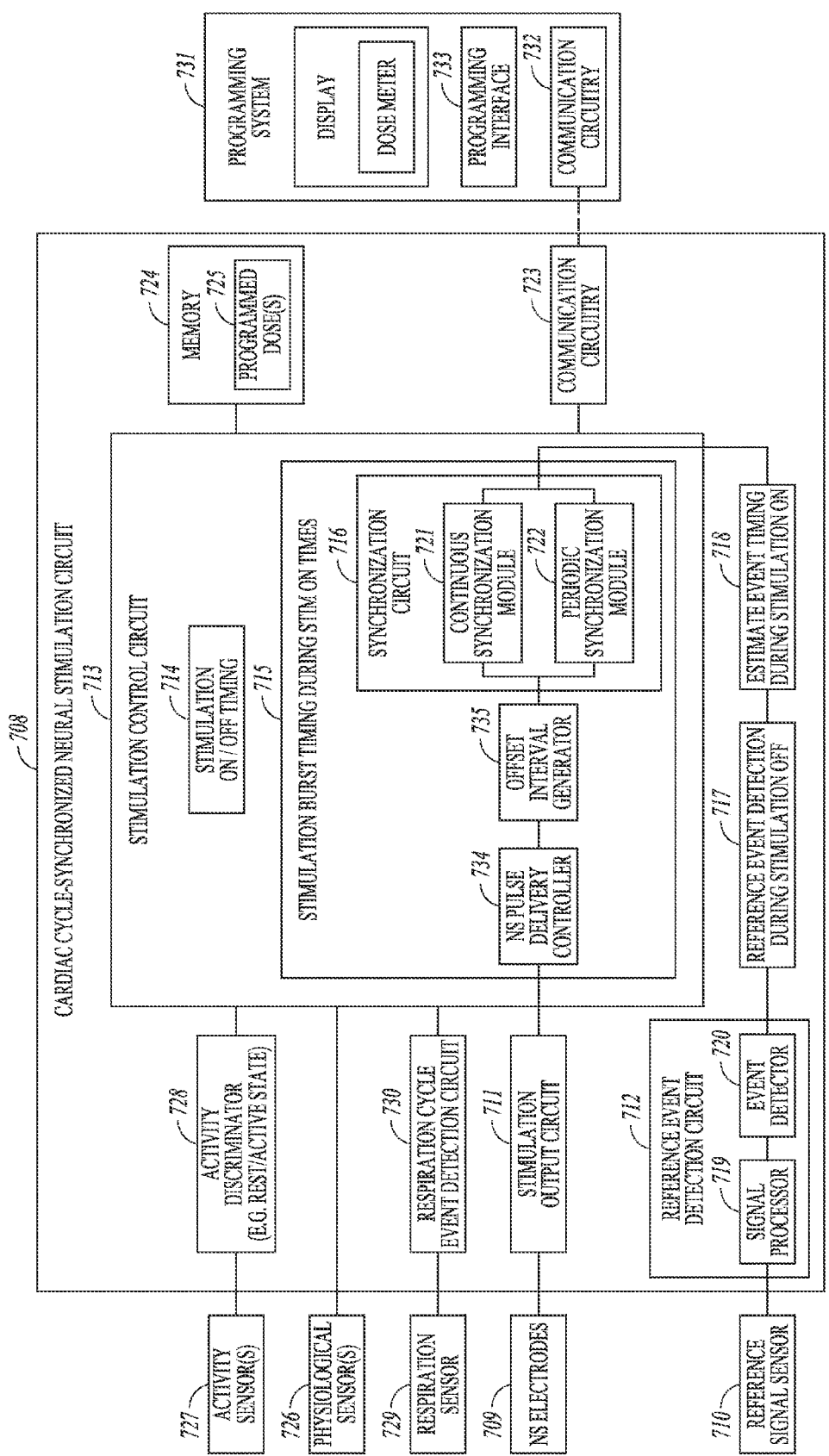
FIG. 7 illustrates an example of a system which may be a more specific embodiment of the system in FIG. 4.

FIG. 7 illustrates an example of a system which may be a more specific embodiment of the system in FIG. 4. The system includes an intuited cardiac cycle-synchronized neural stimulation circuit 708, which may be a specific embodiment of the cardiac cycle-synchronized neural stimulation circuit 408 in FIG. 4. The system may include NS electrodes 709 for use in delivering neural stimulation, and a reference signal sensor 710 for use in detecting a reference within a cardiac cycle. Detection of the reference allows the circuit 708 to estimate synchronized delivering of a burst of NS pulses within the cardiac cycle. The reference signal sensor 710 senses a reference signal indicative of cardiac cycles. The reference signal sensor 710 may be an implantable reference signal sensor. The timing reference event is a recurring feature of the cardiac cycle that is chosen to be a timing reference to which the neural stimulation is synchronized. The intuited cardiac cycle-synchronized neural stimulation circuit 708 may include a stimulation output circuit 711, a reference event detection circuit 712, and a stimulation control circuit 713. The reference event detection circuit 712 receives the reference signal from the reference signal sensor 710 and detects the timing reference event from the reference signal.

The stimulation control circuit 713 controls the delivery of the neural stimulation pulses and includes a stimulation on/off timing module 714, and a stimulation burst timing module 715 with a synchronization circuit 716 to control burst timing during stimulation ON times. The stimulation control circuit 713 may further include a reference event detection module 717 configured to detect reference events during stimulation OFF times, and an estimate event timing module 718 configured to predict, based on the detected reference events during stimulation OFF times, event timing to cardiac cycle(s) during the stimulation ON times. The synchronization circuit 716 may be configured to receive a signal from module 718 to identify an event timing estimate, and use that event timing estimate to timer deliver delivery of the neural stimulation pulses. The stimulation output circuit 711 may be configured to deliver neural stimulation pulses upon receiving a pulse delivery signal from the stimulation burst timing module 715.

The reference event detection circuit 712 may be a specific embodiment of the reference event detection 412 and includes a signal processor 719 and an event detector 720. The signal processor 719 receives the reference signal sensed by the reference signal sensor 710 and processes the reference signal in preparation for the detection of the timing reference events by event detector 720. The event detector 720 may include a comparator having an input to receive the processed reference signal, another input to receive a detection threshold, and an output producing a detection signal indicating a detection of the timing reference signal. In an embodiment, the signal processor 719 processes the reference signal to provide for extraction of the timing reference event based on a single cardiac cycle. In an embodiment, the signal processor 719 includes a filter having a pass-band corresponding to a frequency range of the timing reference event to prevent unwanted activities in the reference signal from being detected by event detector 720. In an embodiment, the signal processor 719 includes a blanking period generator to generate a blanking period that blanks the unwanted activities in the reference signal. This approach is applied when an approximate timing relationship between the timing reference event and the unwanted activities, or an approximate timing relationship between another detectable event and the unwanted activities, is predictable. In an embodiment, the blanking period generator generates a blanking period that blanks cardiac pacing artifacts in the reference signal i.e., unwanted activities caused by delivery of cardiac pacing pulses. In an embodiment, the signal processor 719 includes a timing interval generator to generate a timing interval between an intermediate event and the timing reference event. This approach may be applied when the intermediate event is more easily detectable than the timing reference event and when an approximate timing relationship between the intermediate event and the timing reference event is predictable. In an embodiment, the signal processor 719 processes the reference signal to provide for extraction of the timing reference event based on a plurality of cardiac cycles. In one specific embodiment, the signal processor 719 includes a signal averaging circuit that averages the reference signal over a predetermined number of cardiac cycles before the detection of the timing reference event by event detector 720.

As illustrated in FIG. 7 the intuited cardiac cycle-synchronized neural stimulation circuit 708 may include a reference event detection module 717 for determining a reference event during stimulation OFF times. For example the reference event detection module may average the detected reference events by event detector 720 over a number of cardiac cycles during the stimulation OFF time. The average may be taken over the entire stimulation OFF time, or may be taken over a lesser number of cardiac cycles. The average may be taken using only cardiac cycles at the end of the stimulation OFF time (e.g. the last "n" cardiac cycles, such as but limited to the last four cardiac cycles before the subsequent stimulation ON time begins). The average may be a weighted average, where the cardiac cycles toward the end of the stimulation OFF time are weighted heavier than earlier cardiac cycles. An estimate event timing module 718 may be configured to use the reference event timing from the reference event detection module 717 to provide an estimated event timing during the subsequent ON time(s). The estimated event timing is provided to the stimulation burst timing module 715 for use in timing the stimulation bursts during the stimulation ON times.

The stimulation control circuit 713 may be a more specific embodiment of stimulation control circuit 413 and includes a synchronization circuit 716, an offset interval generator 719 and an NS pulse delivery controller 720. The synchronization circuit 716 may include one or both of a continuous synchronization module 721 and a periodic synchronization module 722. The continuous synchronization module 721 synchronizes the delivery of the neural stimulation pulses to the estimated timing reference event of consecutive cardiac cycles. The periodic synchronization module 722 synchronizes the delivery of the neural stimulation pulses to the estimated timing reference event of selected cardiac cycles on a periodic basis. The offset interval generator 735 produces an offset interval starting with the estimated timing reference event. A pulse delivery controller 734 sends the pulse delivery signal to start a delivery of a burst of a plurality of neural stimulation pulses when the offset interval expires. For example, the pulse delivery controller 734 may send the pulse delivery signal after the estimated timing reference event for each of consecutive cardiac cycles. In an example, the pulse delivery controller 734 sends the pulse delivery signal after the detection of the timing reference event for selected cardiac cycles according to a predetermined pattern or programmed schedule, such as on a periodic basis. The illustrated system may also include NS electrodes 709 for use in stimulating a neural target, communication circuitry 723 and memory 724. The memory 724 may include instructions to be operated on to provide various functions of the system. The memory 724 may also include programmed NS dose(s) 725. The illustrated system may also include physiological sensor(s) 726, activity sensor(s) 727, and an activity discriminator 728 for use in determining whether the activity sensor(s) 727 are sensing that the patient is in a particular activity state (e.g. rest/active). The system may also include respiration sensor(s) 729 and a respiration cycle event detection circuit 730 for use in determining reference event(s) in the respiratory cycle, which may be used to control timing and intensity of the neural stimulation bursts. The illustrated system may also include a programming system 731 that has communication circuitry 732 for use in communicating with communication circuitry 723 and a programming interface 733 for use in programming the neural stimulation delivered from the stimulation control circuit 713. The programming system 731 may also include a display, and may be configured to provide an indication to the physician how much stimulation is being delivered over a period of time. This indication may be referred to as a dose meter. The dose meter informs the physician how much stimulation (e.g. number of pulses, or total charge delivered) is or will be delivered. Various combinations of pulse parameters can be displayed to provide a calculated or estimated dose. For example, a product of amplitude and pulse number may be used to provide an estimate of the dose over the period of time. By way of example but not limitation, the period of time may be an hour or a day. Furthermore, the dose meter may provide current dose information that reflects the dose delivered using the currently-programmed stimulation parameters, and may also provide dose information for proposed stimulation parameters which allows the physician to confirm the dose information before programming those parameters into the memory 724 of the cardiac cycle-synchronized neural stimulation circuit 708.

Figure 8:
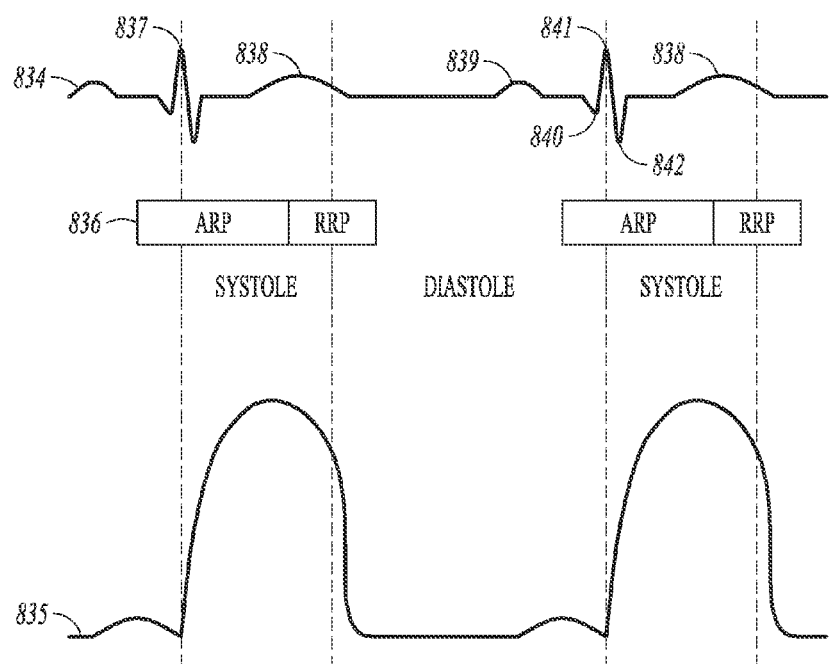
FIG. 8 illustrates a general relationship between an electrocardiogram (ECG), a pressure waveform within a blood vessel (e.g. pulmonary artery) and the refractory period of the heart during systolic and diastolic portions of a cardiac cycle.

FIG. 8 illustrates a general relationship between an electrocardiogram (ECG) 834, a pressure waveform 835 within a blood vessel (e.g. pulmonary artery) and the refractory period 836 of the heart during systolic and diastolic portions of a cardiac cycle. Systole is the portion of the cardiac cycle when the heart contracts to force blood through the circulatory system. Diastole is the portion of the cardiac cycle when the heart expands to fill with blood. Blood pressure increases during systole.

Figure 9:
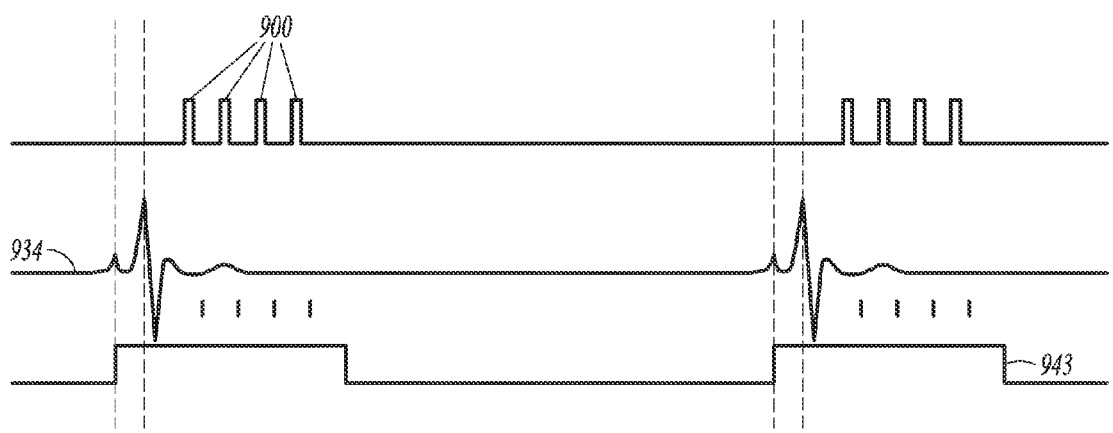
FIG. 9 illustrates an example of a NS burst of NS pulses delivered during an NS window that generally corresponds to at least a portion of the refractory period of the heart as illustrated by the ECG signal.

The cardiac refractory period 836 is separated into an absolute refractory period (ARP) and a relative refractory period (RRP). During the absolute refractory period, a new action potential cannot be elicited during the absolute refractory period but may be elicited with a greater than normal stimulus during the relative refractory period. The refractory period generally begins with the QRS waveform 837 and extends through the T wave 838. Various detectable cardiac events within the cardiac cycle may be used to time the delivery of NS bursts. Examples of such detectable cardiac events include but are not limited to the P wave 839, Q wave 840, R wave 841, S wave 842 or T wave 838, or different detectable heart sounds for example. Some embodiments may time the delivery of the NS burst of NS pulses to occur during at least a portion of the refractory period (i.e. during at least a portion of the absolute and/or relative refractory periods). For example, baroreceptors sense pressure and elicit a baroreflex response. Neural stimulation to elicit a baroreflex response may be estimated to occur during the refractory period to augment the natural baroreflex response during systole. FIG. 9 illustrates an example of a NS burst of NS pulses 900 delivered during an NS window 943 that generally corresponds to at least a portion of the refractory period of the heart as illustrated by the ECG signal 934. In some embodiments, the delivery of the NS burst of NS pulses may be estimated to occur during diastole to reduce the pulsation of the naturally-elicited baroreflex response.

Figure 10:
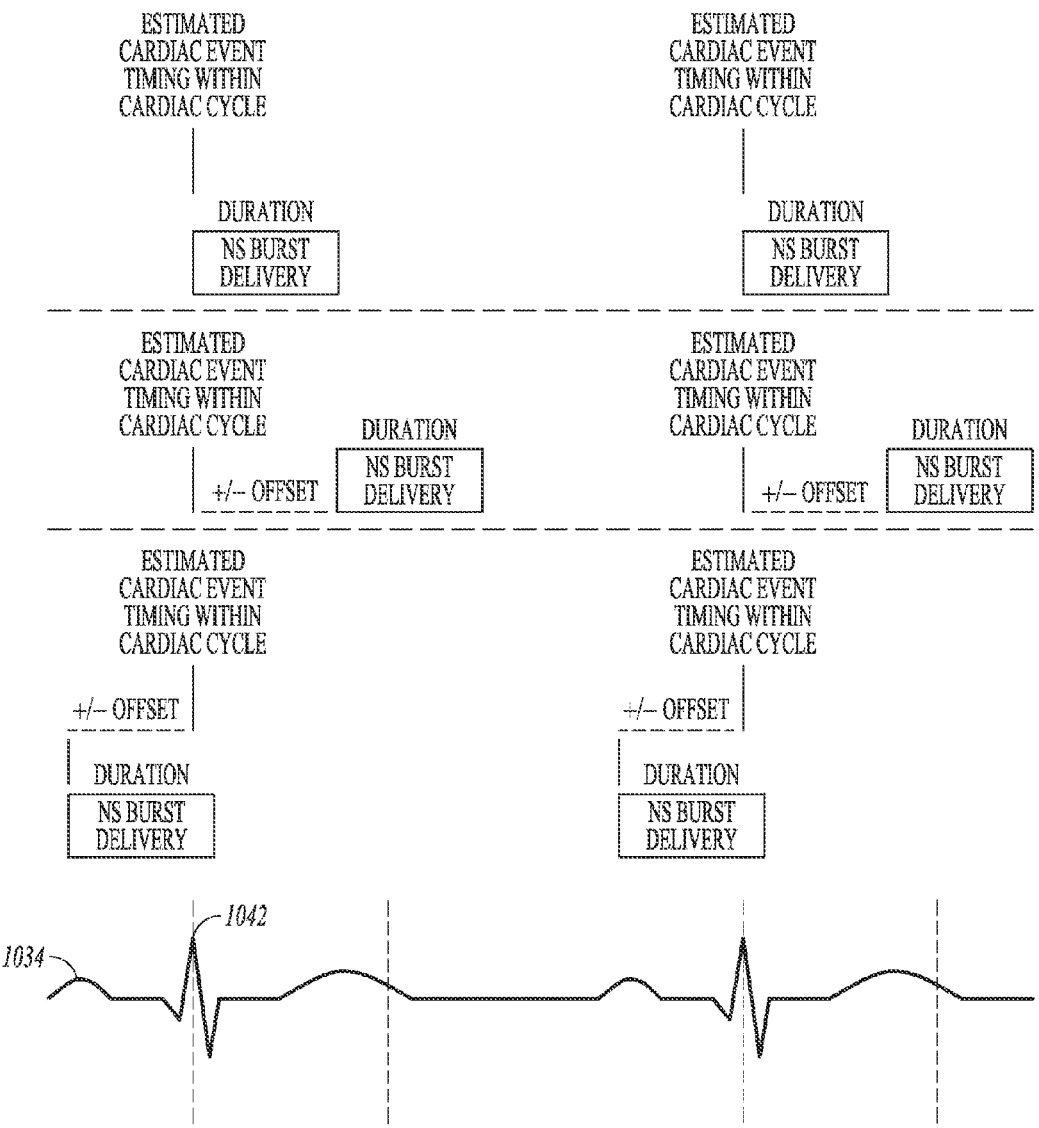
FIG. 10 illustrates, by way of example and not limitation, some embodiments of NS burst timing.
Figure 11:
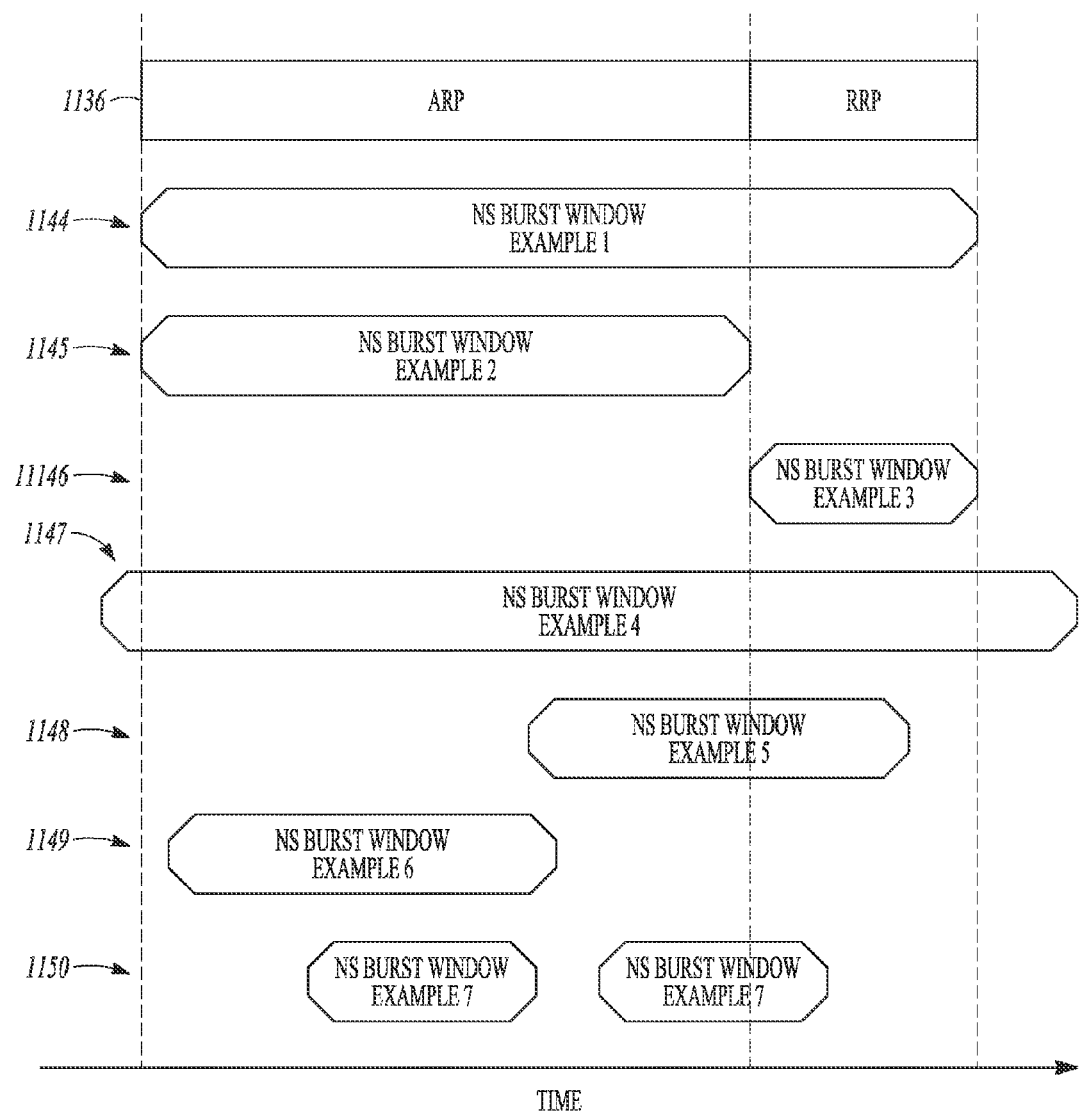
FIG. 11 illustrates some NS burst timing with respect to the refractory period, by way of examples and not limitation.

FIG. 10 illustrates, by way of example and not limitation, some embodiments of NS burst timing. In a first example, the NS burst is delivered during a window of time beginning with the estimated cardiac event. The initiation of the NS burst may begin with the detected cardiac cycle. In the illustrated examples, the cardiac event corresponds with the R wave 1041 in the ECG signal 1034. The duration of the NS burst may be a programmable parameter. The duration of the NS burst may be dynamically adjusted based on the predicted rate. An example of dynamic adjustment based rate can be found in U.S. application Ser. No. 61/912,274) filed on the same date as the present application, and entitled "Dosed Delivery of Autonomic Modulation Therapy", which application has been incorporated by reference herein in its entirety. In a second example, the NS burst is initiated an offset period of time after the estimated cardiac event. In a third example, the NS burst is initiated at offset period of time before the estimated cardiac event. FIG. 11 illustrates some NS burst timing with respect to the refractory period 1136, by way of examples and not limitation. It is understood that, in the present application, the NS burst windows may be estimated burst windows based on estimated cardiac timing during the NS ON portion of the duty cycle. In a first example 1144, the NS burst window, within which the burst of NS pulses may be delivered, is generally begins as the refractory period begins and ends when the refractory period ends. In a second example 1145, the NS burst window, within which the burst of NS pulses may be delivered, generally begins as the absolute refractory period beings and ends as the absolute refractory period ends. In a third example 1146, the NS burst window, within which the burst of NS pulses may be delivered, generally begins at the beginning of the relative refractory period and ends as the relative refractory period ends. In a fourth example 1147, the NS burst window, within which the burst of NS pulses may be delivered, may begin before the refractory period begins and/or may end after the refractory period ends. In a fifth example 1148, the NS burst window, within which the burst of NS pulses may be delivered, generally begins and ends within the refractory period. In the sixth example 1149, the NS burst window, within which the burst of NS pulses may be delivered, generally begins and ends within the absolute refractory period. In a seventh example 1150, more than one NS burst window may be provided within the refractory period. Thus, by way of example and not limitation and as will be understood by those of ordinary skill in the art upon reading and comprehending this document, various embodiments may time the burst of NS pulses may be timed to cover systole. Systole was generally illustrated in FIGS. 8 and 10, for example. The ARP and RRP are dependent on the cardiac rate. Further, in some embodiments for example, the burst duration may be dependent on the cardiac rate. For example, a number of pulses may be evenly distributed over the burst duration. A pulse-to-pulse interval may be adjusted for a given burst duration if the number of pulses per cardiac cycle change. In another example, the pulse-to-pulse interval may remain the same, while the burst duration is modified which may affect timing of the start and/or stop times for the burst of pulses. Thus, for example, various embodiments may dynamically adjust, based on a predicted cardiac rate, an NS burst duration, or a number of pulses per NS burst, or a pulse-to-pulse interval with the NS burst.

Figure 12:
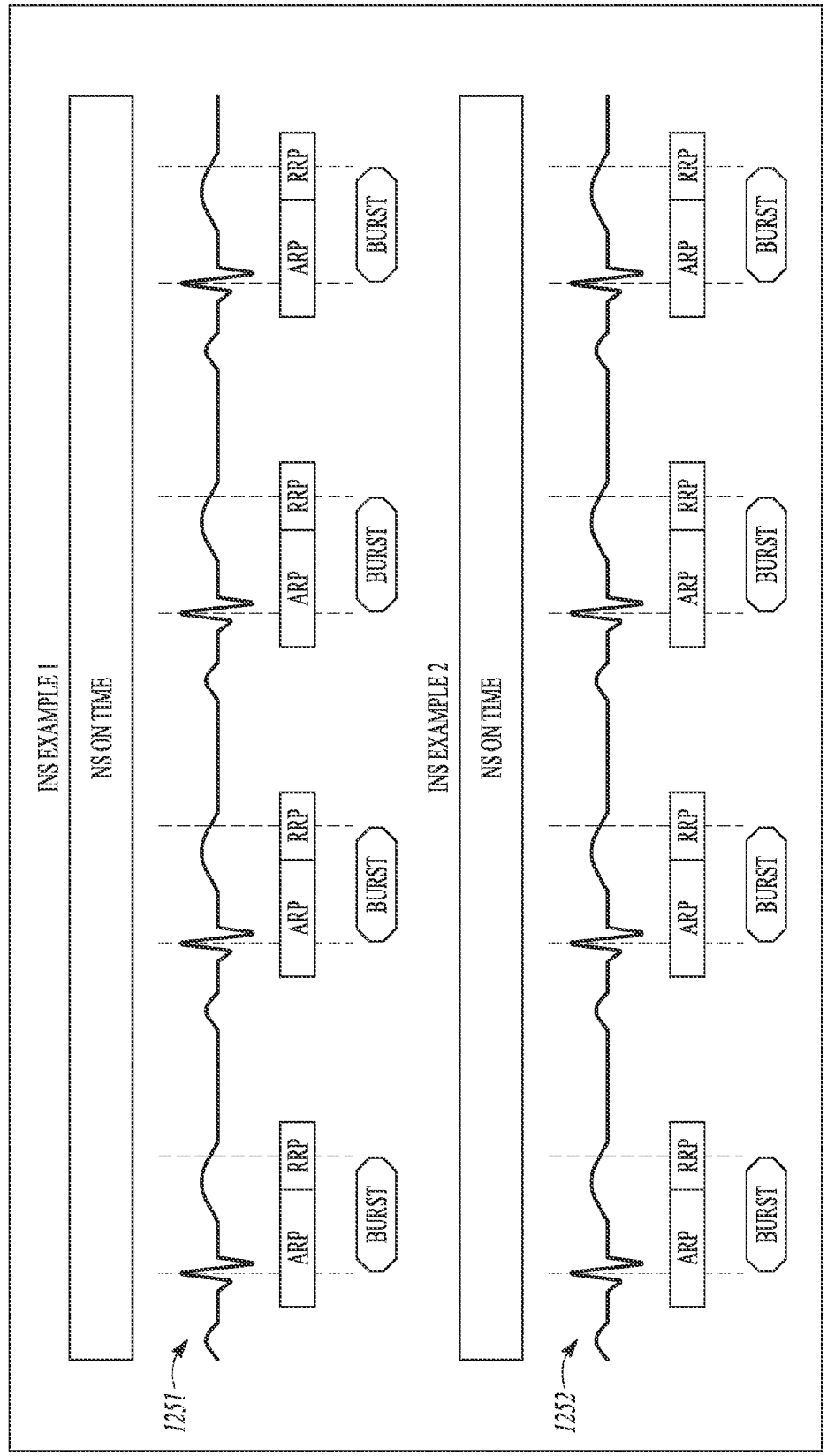
FIG. 12 illustrates some NS burst timing with respect to cardiac cycles.

FIG. 12 illustrates some NS burst timing with respect to cardiac cycles. Again, it is understood that, in the present application, the NS burst timing may be estimated based on estimated cardiac timing during the NS ON portion of the duty cycle. In a first example 1251, a NS burst of NS pulses is delivered during every cardiac cycle. In a second example 1252, a NS burst of NS pulses is delivered only is some of the cardiac cycles, and is not delivered in other cycle. For example, the NS burst may be delivered every other cardiac cycle. The determination of which cardiac cycles within which to deliver a NS burst may be based on a timer. For example, after expiration of a timer a NS burst may be delivered during each of the next one or more cardiac cycles; or after expiration of a timer a pattern of cardiac cycles a NS burst may be delivered for a pattern of cardiac cycles (e.g. every N cardiac cycles). The determination of which cardiac cycles within which to deliver a NS burst may be based on a sensed physiological parameter.

FIGS. 13-17 illustrate various embodiments for delivering a NS burst of pulses at estimated times within a cardiac cycle. These processes may be implemented, for example, using any of the systems illustrated in FIGS. 4 and 7. The processes may be implemented using hardware, software and/or firmware.

Figure 13:
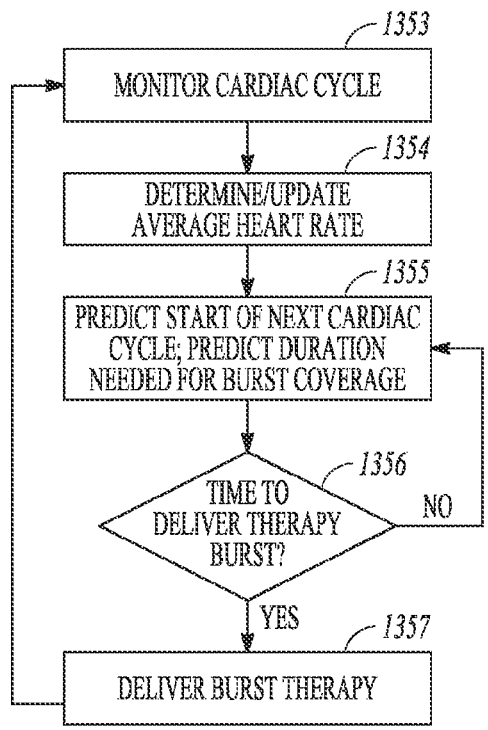
FIG. 13 illustrates a method for delivering a NS burst of pulses at a predicted time within a cardiac cycle.

FIG. 13 illustrates a method for delivering a NS burst of pulses at a predicted time within a cardiac cycle. At 1353, cardiac activity is monitored to monitor the cardiac cycle. The cardiac activity may be monitored using a variety of means such as, but not limited to, heart rate sensors, accelerometer sensors, acoustic sensors, etc. At 1354 the monitored cardiac activity is used to determine an average heart rate for at least a portion of time when neural stimulation is not being delivered. If heart rate has already been determined previously, then the average heart rate may be updated. At 1355 the average heart rate is used to predict the start of a subsequent cardiac cycle. This cardiac cycle may be the next cardiac cycle. This cardiac cycle may be the first cardiac cycle or other cardiac cycles during the stimulation ON portion of the duty cycle. Also, the duration of the burst is predicted. This information is used to determine an estimated time when to deliver the burst of neural stimulation. Once it is determined that it is time to deliver the therapy burst, as represented at 1356, the process proceeds to deliver the burst therapy at 1357. The estimated burst timing may be provided for multiple cardiac cycles within a Stimulation ON portion before returning to monitor cardiac cycles without neural stimulation at 1353. Some embodiments may continue to monitor cardiac cycles during the neural stimulation to confirm that actual stimulation timing within the cardiac cycle appears to reasonably coincide with the estimated burst timing. Some embodiments may incorporate a "fallback" therapy delivery mode where, if cannot accurately predict next cardiac cycle, then neural stimulation pulses may be delivered continuously for the remainder of ON portion of duty cycle. It is currently believed that estimated timing does not need 100% accurate in estimating the cardiac cycle for AMT.

Figure 14:
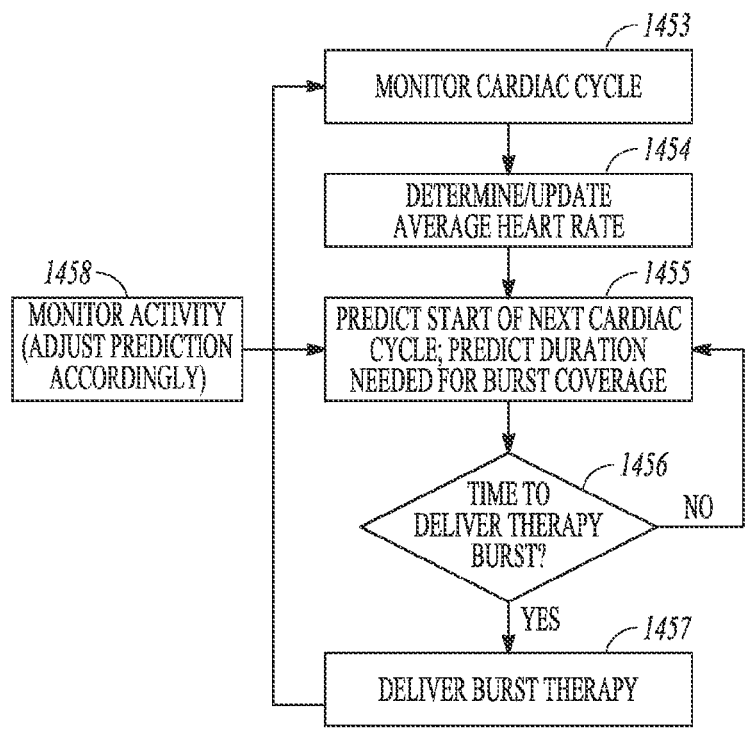
FIG. 14 illustrates a method for delivering a NS burst of pulses at a predicted time a cardiac cycle, similar to FIG. 13, but that also continues to update the predicted start of the next cardiac cycle within which the neural stimulation pulses are delivered.

FIG. 14 illustrates a method for delivering a NS burst of pulses at a predicted time a cardiac cycle, similar to FIG. 13, but that also continues to update the predicted start of the next cardiac cycle within which the neural stimulation pulses are delivered. At 1453, cardiac activity is monitored to monitor the cardiac cycle. At 1454 the monitored cardiac activity is used to determine an average heart rate for at least a portion of time when neural stimulation is not being delivered. If heart rate has already been determined previously, then the average heart rate may be updated. At 1455 the average heart rate is used to predict the start of a subsequent cardiac cycle. This cardiac cycle may be the next cardiac cycle. This cardiac cycle may be the first cardiac cycle or other cardiac cycles during the stimulation ON portion of the duty cycle. Also, the duration of the burst is predicted. This information is used to determine an estimated time when to deliver the burst of neural stimulation. The cardiac activity may continue to be monitored, as generally illustrated at 1458, while waiting for the predicted start of the next cardiac cycle for which neural stimulation will be delivered. Once it is determined that it is time to deliver the therapy burst, as represented at 1456, the process proceeds to deliver the burst therapy at 1457. The estimated burst timing may be provided for multiple cardiac cycles within a Stimulation ON portion of the duty cycle before returning to monitor cardiac cycles without neural stimulation at 1453. Some embodiments may continue to monitor cardiac cycles during the neural stimulation to confirm that actual stimulation timing within the cardiac cycle appears to reasonably coincide with the estimated burst timing. Thus, the predictions may be further adjusted during the NS ON time based on the monitored cardiac activity. For example, a recent trend in heart rate (increasing heart rate or decreasing heart rate) may trigger an adjustment. Furthermore, other sensor(s) may be used (activity, accelerometer, minute ventilation, etc.) may be used individually or combined to provide a blended sensor for use in adjusting the estimate when the next cardiac cycle(s) occurs. As heart rate may change by the nerve stimulation, the use of other sensors either alone or in conjunction with the heart rate sensor during the ON portion of the duty cycle may improve the prediction when the next cardiac cycle(s) occur.

As the cardiac rate increases, the cardiac cycle decreases and the desired therapy delivery window (see NS window 943 in FIG. 9 for example) may decrease with the decreasing cardiac cycle. Therefore, to maintain therapy delivery within desired time frame, some embodiments may automatically increase the pulse frequency of the NS pulses within the burst delivery and/or reduce the number of pulses delivered.

The rhythmic bursting of efferent activity is synchronous with ventilatory movements. It is also affected by the time of day. A respiratory sensor, such as a minute ventilation (MV) or other sensor, may be used to monitor respiration. According to some embodiments, neural stimulation may be delivered only in a predicted respiratory time window. In some embodiments, neural stimulation may only be delivered in predicted cardiac cycles within the predicted respiratory time window. In some embodiments, the stimulation in the predicted cardiac cycle is changed during different phases of predicted respiratory windows. In some embodiments, the stimulation in the predicted cardiac cycle is changed based on circadian rhythm.

Figure 15:
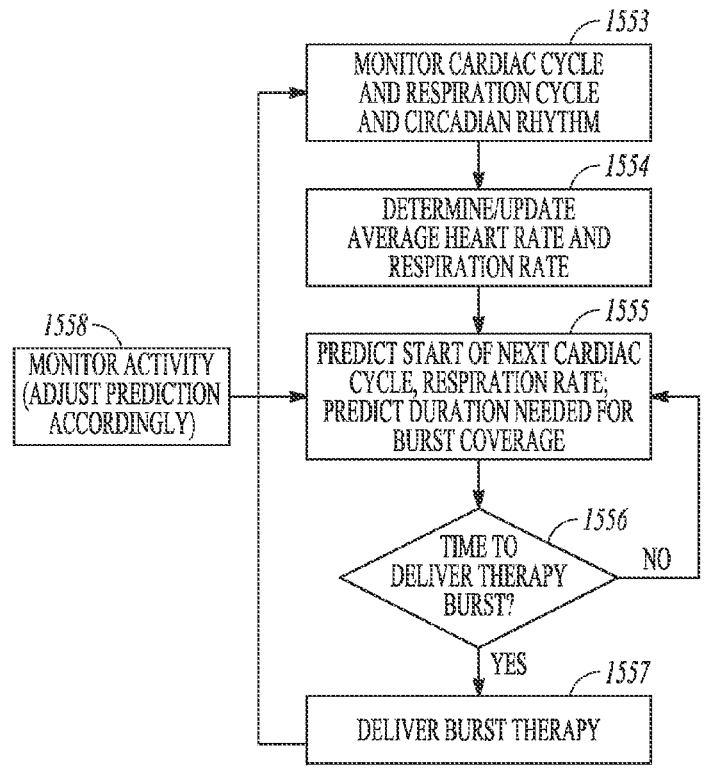
FIG. 15 illustrates a method for delivering a NS burst of pulses at a predicted time a cardiac cycle, similar to FIG. 14, but that also monitors respiration cycle and in some embodiments also monitors a circadian rhythm.

FIG. 15 illustrates a method for delivering a NS burst of pulses at a predicted time a cardiac cycle, similar to FIG. 14, but that also monitors respiration cycle and in some embodiments also monitors a circadian rhythm. At 1553, cardiac activity is monitored to monitor the cardiac cycle. Additionally, a respiration cycle may also be monitored. In some embodiments, a circadian rhythm is monitored. At 1554 the monitored cardiac activity is used to determine an average heart rate for at least a portion of time when neural stimulation is not being delivered. If heart rate has already been determined previously, then the average heart rate may be updated. The monitored respiration cycle is used to determine an average respiration rate. This cardiac cycle may be the next cardiac cycle, or may be the first cardiac cycle or other cardiac cycles during the stimulation ON portion of the duty cycle. At 1555 the average heart rate is used to predict the start of a subsequent cardiac cycle. The average respiration rate is used to predict the respiration rate during the next stimulation ON time. Also, the duration of the burst is predicted. This information is used to determine an estimated time when to deliver the burst of neural stimulation. The cardiac activity may continue to be monitored, as generally illustrated at 1558, while waiting for the predicted start of the next cardiac cycle for which neural stimulation will be delivered. Once it is determined that it is time to deliver the therapy burst, as represented at 1556, the process proceeds to deliver the burst therapy at 1557. The estimated burst timing may be provided for multiple cardiac cycles and respiration cycles within a Stimulation ON portion before returning to monitor cardiac cycles without neural stimulation at 1553. Some embodiments may continue to monitor cardiac cycles during the neural stimulation to confirm that actual stimulation timing within the cardiac cycle appears to reasonably coincide with the estimated burst timing.

The present subject matter may maintain therapy effectiveness with reduced power consumption, and may closely mimic natural sympathetic nerve activity. The initial algorithm for predicting the next cardiac cycle and burst duration can be relatively crude. A learn mode may be used to improve the prediction. The next prediction may be dynamically adjusted if the star of a new cardiac cycle is sensed outside the predicted delivery window rather than just basing the next prediction on heart rate during OFF period.

Figure 16:
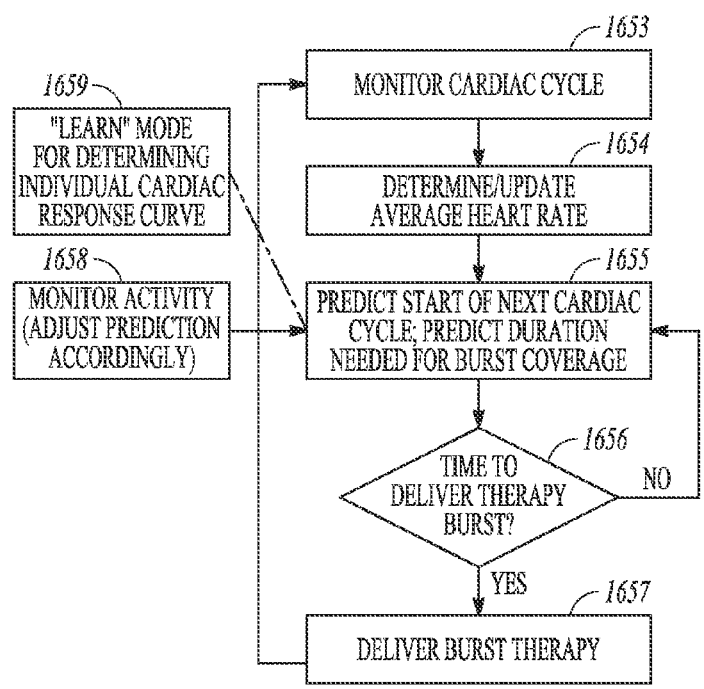
FIG. 16 illustrates a method for delivering a NS burst of pulses at a predicted time a cardiac cycle, similar to FIG. 14, but that also incorporates a learn mode.

FIG. 16 illustrates a method for delivering a NS burst of pulses at a predicted time a cardiac cycle, similar to FIG. 14, but that also incorporates a learn mode 1659. At 1653, cardiac activity is monitored to monitor the cardiac cycle. Additionally, a respiration cycle may also be monitored. In some embodiments, a circadian rhythm is monitored. At 1654 the monitored cardiac activity is used to determine an average heart rate for at least a portion of time when neural stimulation is not being delivered. If heart rate has already been determined previously, then the average heart rate may be updated. The monitored respiration cycle is used to determine an average respiration rate. This cardiac cycle may be the next cardiac cycle, or may be the first cardiac cycle or other cardiac cycles during the stimulation ON portion of the duty cycle. At 1655 the average heart rate is used to predict the start of a subsequent cardiac cycle. The average respiration rate is used to predict the respiration rate during the next stimulation ON time. Also, the duration of the burst is predicted. This information is used to determine an estimated time when to deliver the burst of neural stimulation. The cardiac activity may continue to be monitored, as generally illustrated at 1658, while waiting for the predicted start of the next cardiac cycle for which neural stimulation will be delivered. As illustrated at 1659 a learn mode may be used to determine an individual cardiac response curve. Thus, for example, if the actual cardiac cycle is different from the predicted cardiac cycle. The learn mode can thus improve the prediction of the cardiac event timing. Once it is determined that it is time to deliver the therapy burst, as represented at 1656, the process proceeds to deliver the burst therapy at 1657. The estimated burst timing may be provided for multiple cardiac cycles and respiration cycles within a Stimulation ON portion before returning to monitor cardiac cycles without neural stimulation at 1653. Some embodiments may continue to monitor cardiac cycles during the neural stimulation to confirm that actual stimulation timing within the cardiac cycle appears to reasonably coincide with the estimated burst timing.

Some embodiments modify the neural stimulation for circadian rhythm, as sympathetic tone may increase in early morning hours (and/or at other times). A reduced number of pulses in a burst may reduce side effects such as coughing. A physician or patient input could further refine parameters. For example, a patient may indicate higher amplitudes are tolerable during activity or lower amplitudes tolerable during period before sleep, and a physician may upload pacing parameters from concomitant pulse generator to stimulate myocardia for more precise predictions during cardiac rhythm management (CRM) pacing.

Figure 17:
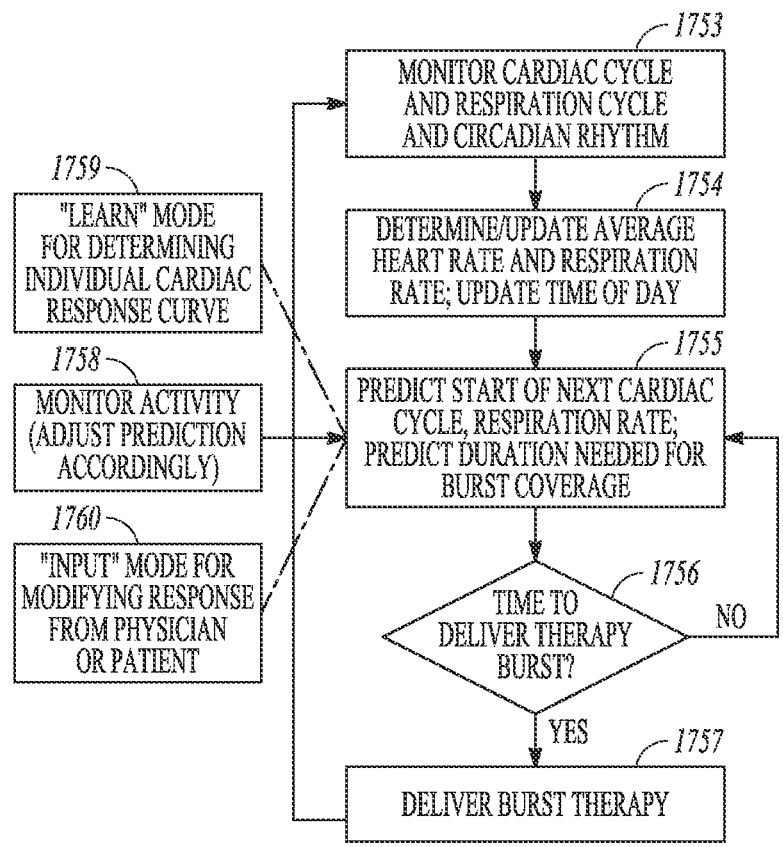
FIG. 17 illustrates a method for delivering a NS burst of pulses at a predicted time a cardiac cycle, similar to FIG. 16, but that also incorporates an input mode.

FIG. 17 illustrates a method for delivering a NS burst of pulses at a predicted time a cardiac cycle. At 1753, cardiac activity is monitored to monitor the cardiac cycle. Additionally, a respiration cycle and circadian rhythm may also be monitored. At 1754 the monitored cardiac activity is used to determine an average heart rate for at least a portion of time when neural stimulation is not being delivered. If heart rate has already been determined previously, then the average heart rate may be updated. The monitored respiration cycle is used to determine an average respiration rate. This cardiac cycle may be the next cardiac cycle, or may be the first cardiac cycle or other cardiac cycles during the stimulation ON portion of the duty cycle. The time of day may be updated too. At 1755 the average heart rate is used to predict the start of a subsequent cardiac cycle. The average respiration rate is used to predict the respiration rate during the next stimulation ON time. Also, the duration of the burst is predicted. This information is used to determine an estimated time when and how long to deliver the burst of neural stimulation. The cardiac activity may continue to be monitored, as generally illustrated at 1758, while waiting for the predicted start of the next cardiac cycle for which neural stimulation will be delivered. As illustrated at 1759 a learn mode may be used to determine an individual cardiac response curve. Thus, for example, if the actual cardiac cycle is different from the predicted cardiac cycle. The learn mode can thus improve the prediction of the cardiac event timing. As illustrated at 1760, a physician or patient may provide an input to modify the response for delivering neural stimulation. For example, the modification may be based on circadian rhythm. Once it is determined that it is time to deliver the therapy burst, as represented at 1756, the process proceeds to deliver the burst therapy at 1757. The estimated burst timing may be provided for multiple cardiac cycles and respiration cycles within a Stimulation ON portion before returning to monitor cardiac cycles without neural stimulation at 1653. Some embodiments may continue to monitor cardiac cycles during the neural stimulation to confirm that actual stimulation timing within the cardiac cycle appears to reasonably coincide with the estimated burst timing.

It can be technically challenging for the sensing circuitry within an implanted system to consistently detect cardiac activity while the therapy circuitry of the system is delivering a burst. The prediction may be adjusted during the stimulation ON portion of the duty cycle if an intrinsic or PVC is detected between VNS delivery. A detected intrinsic sinus beat may indicate that the prediction was wrong because interference may prevent the system from normally detecting cardiac activity during the neural stimulation in a reliable manner. A detected intrinsic sinus beat may indicate that the prediction was wrong because of the prediction algorithms themselves are not 100% accurate at all times and could get less accurate as time progresses over a longer ON portion. A PVC will alter the timing of subsequent cardiac events and the prediction may need to be adjusted and updated upon detection of a PVC. Detection of a PVC may require suspending therapy delivery until a new average is acquired and the remaining ON portion may be adjusted accordingly to account for the time needed to acquire the new average. Detected intrinsic tachycardia beats may require adjusting the prediction to the new average reflective of the tachycardia or therapy may be suspended until the tachycardia has resolved or therapy may be transitioned to therapy specific to treatment of tachycardia. If a sense detect is corrupted by noise, the system may respond differently for a short period of noise vs. a long period of noise. For example, the average cardiac rate may be adjusted if one or two cardiac cycles are corrupted by noise. A previously determined average can be re-used if one or a few stimulation OFF portions of the duty cycle are corrupted by noise. If the system is unable to obtain reliable inputs for making predictions, the system can fall back to a programmed neural stimulation protocol that is not synchronized to a portion of a cardiac cycle. Such a programmed neural stimulation protocol may be, by way of example and not limitation, about 10 seconds ON and 50 seconds OFF.

Some embodiments combine NS functions with an implantable cardioverter or defibrillator. The combined system may allow detection of ventricular fibrillation (VF) or ventricular tachycardia (VT) by keeping open CRM sensing windows between NS deliveries. NS, if delivered over the PQRS phase, could induce noise that could challenge normal sinus rhythm sensing by the CRM leads. However, it may not be necessary to detect normal sinus rhythm beats during NS ON time (i.e. not a pacer dependent patient but a MADIT II indicated patient). VF or VT may be detected between the NS deliveries. If a suspected VF or VT is detected then NS may be halted or dropped during the next predicted period(s). If, rather than being an actual VF or VT, the suspected VF or VT is a normal sinus beat that broke through because prediction was off or is a premature ventricular contraction (PVC) and normal sinus rhythm returns, then the system may return to predicting and delivering for the remainder of the NS ON time. The sensing window for VF/VT may be maintained.

The above detailed description is intended to be illustrative, and not restrictive. Other embodiments will be apparent to those of ordinary skills in the art upon reading and understanding the above description. The scope of the disclosure should, therefore, be determined with references to the appended claims, along with the full scope of equivalents to which such claims are entitled.

What is claimed is:

1. A method, comprising:
    delivering intermittent neural stimulation (INS) therapy to an autonomic neural target of a patient, the INS therapy including neural stimulation (NS) ON times alternating with NS OFF times, wherein delivering INS therapy includes delivering at least one NS burst of NS pulses during each of the NS ON times, wherein for a given NS OFF time and subsequent NS ON time, delivering INS therapy includes:
    monitoring a plurality of cardiac cycles during the NS OFF time;
    using the monitored plurality of cardiac cycles to predict cardiac event timing during the subsequent NS ON time; and
    controlling delivery of the INS therapy using the predicted cardiac event timing to time NS burst delivery of at least one NS burst for the subsequent NS ON time based on the predicted cardiac event timing.

2. The method of claim 1, wherein controlling delivery of the INS therapy includes using the predicted cardiac event timing to time NS burst delivery to deliver NS pulses during at least a portion of a predicted refractory period time during the subsequent ON time.

3. The method of claim 1, wherein for the given NS OFF time and subsequent NS ON time:
    delivering INS therapy includes delivering more than one NS burst during the subsequent NS ON time;
    using the monitored plurality of cardiac cycles includes using the monitored plurality of cardiac cycles to predict cardiac event timing for more than one of the plurality of cardiac cycles during the sequent NS ON time; and
    controlling delivery of the INS therapy includes using the predicted cardiac event timing for more than one of the plurality of cardiac cycles during the subsequent ON time to time NS burst delivery of more than one NS burst during the subsequent ON time.

4. The method of claim 1, wherein delivering INS therapy includes:
    predicting cardiac event timing in each two or more successive cardiac cycles during the subsequent NS ON time using the monitored plurality of cardiac cycles during the NS OFF time; and
    delivering at least one burst of NS burst of NS pulses for each of the two or more successive cardiac cycles based on the cardiac timing.

5. The method of claim 1, wherein delivering INS therapy includes:
    predicting cardiac timing in each of two or more non-successive cardiac cycles during the subsequent NS ON time using the monitored plurality of cardiac cycles during the NS OFF time; and
    delivering at least one burst of NS pulses for each of the two or more non-successive cardiac cycles based on the cardiac timing, and not delivering NS pulses during one or more other cardiac cycles between the non-successive cardiac cycles.

6. The method of claim 1, wherein each of the NS ON times correspond to a respective cardiac event.

7. The method of claim 1, wherein monitoring the plurality of cardiac cycles during the NS OFF time includes sensing heart sounds to monitor the plurality of cardiac cycles.

8. The method of claim 1, wherein monitoring the plurality of cardiac cycles during the NS OFF time includes sensing pulse pressure.

9. The method of claim 1, wherein monitoring the plurality of cardiac cycles during the NS OFF time includes using a wide sense vector to remotely monitor the plurality of cardiac cycles.

10. The method of claim 1, wherein monitoring the plurality of cardiac cycles during the NS OFF time includes using a cardiac sensing lead to monitor the plurality of cardiac cycles.

11. The method of claim 1, wherein:
monitoring the plurality of cardiac cycles during the NS OFF time includes determining an average heart rate for two or more cardiac cycles during the NS OFF time; and
using the monitored plurality of cardiac cycles to predict cardiac event timing during the subsequent NS ON time includes using the average heart rate to predict cardiac event timing during the subsequent NS ON time.

12. The method of claim 1, wherein:
monitoring the plurality of cardiac cycles during the NS OFF time includes determining an average heart rate for four cardiac cycles during the NS OFF time; and
using the monitored plurality of cardiac cycles to predict cardiac event timing during the subsequent NS ON time includes using the average heart rate to predict cardiac event timing during the subsequent NS ON time.

13. The method of claim 1, wherein delivering INS therapy includes delivering a chronic INS therapy to treat a chronic condition.

14. The method of claim 13, wherein the chronic INS therapy includes a hypertension therapy.

15. The method of claim 13, wherein the chronic INS therapy includes a heart failure therapy.

16. The method of claim 1, wherein the INS therapy includes approximately 10 second NS ON times alternating with approximately 50 second NS OFF times.

17. The method of claim 1, wherein the INS therapy includes NS ON times within a range of approximately 1 second to 6 seconds, and NS OFF times within a range of approximately 5 seconds to 30 seconds.

18. The method of claim 1, wherein:
controlling delivery of the INS therapy using the predicted cardiac event timing includes timing delivery of NS pulses during at least a portion of an absolute refractory period, a relative refractory period, or both the absolute and relative refractory period; and
delivering the at least one NS burst of NS pulses during each of the NS ON times includes:
dynamically adjusting, based on a predicted cardiac rate, an NS burst duration, or a number of pulses per NS burst or a pulse-to-pulse interval with the NS burst; or
dynamically adjusting timing for delivering NS pulses in response to a premature ventricular contraction (PVC).

19. A system for delivering neural stimulation to an autonomic neural target of a patient, the system comprising:
a cardiac cycle monitor configured to monitor cardiac cycles;
a neural stimulator configured to deliver neural stimulation to the autonomic neural target; and
a controller configured to control the neural stimulator to deliver intermittent neural stimulation (INS) therapy to the autonomic neural target, the INS therapy including neural stimulation (NS) ON times alternating with NS OFF times, wherein in delivering INS therapy the controller and the neural stimulator cooperate to deliver at least one NS burst of NS pulses during each of the NS ON times;
the controller, the neural stimulator and the cardiac cycle monitor configured to cooperate to implement a process to control NS burst timing where the process comprises:
monitoring a plurality of cardiac cycles during a given NS OFF time;
using the monitored plurality of cardiac cycles during the given NS OFF time to predict cardiac event timing during a subsequent NS ON time; and
controlling delivery of the INS therapy using the predicted cardiac event timing to time NS burst delivery of at least one NS burst for the subsequent NS ON time based on the predicted cardiac event timing.

20. The system of claim 19, wherein the INS therapy more than one NS burst during the NS ON time, and the process implemented through cooperation of the controller, the neural stimulator and the cardiac cycle monitor includes:
using the monitored plurality of cardiac cycles to determine an average heart rate, and using the average heart rate to predict cardiac timing for more than one cardiac cycle during the subsequent NS ON time; and
using the predicted cardiac timing for the more than one cardiac cycle during the subsequent ON time to time NS burst delivery for each of the more than one cardiac cycle during the subsequent ON time.

\* \* \* \* \*